United States Patent
Taha et al.

(12)

(10) Patent No.: US 6,304,772 B1
(45) Date of Patent: Oct. 16, 2001

(54) METHOD AND APPARATUS FOR AUTOMATICALLY DETECTING AND INTERPRETING PACED ELECTROCARDIOGRAMS

(75) Inventors: Basel Hasan Taha, Menomonee Falls; Shankara Bonthu Reddy, Cedarburg, both of WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 0 days.

(21) Appl. No.: 09/385,792

(22) Filed: Aug. 30, 1999

(51) Int. Cl.[7] ................................................. A61B 5/0402
(52) U.S. Cl. ............................................. 600/510; 128/901
(58) Field of Search ...................... 600/509, 510; 607/9, 27, 28, 31, 32, 60; 128/901

(56) References Cited

U.S. PATENT DOCUMENTS

| | | | |
|---|---|---|---|
| 4,094,310 | * 6/1978 | McEachern et al. | 607/5 |
| 5,413,593 | 5/1995 | Spinelli et al. | 607/27 |
| 5,540,232 | 7/1996 | Laney et al. | 128/697 |
| 5,660,184 | 8/1997 | Donehoo et al. | 128/696 |
| 5,771,898 | 6/1998 | Marinello | 128/697 |

* cited by examiner

Primary Examiner—Jeffrey R. Jastrzab
(74) Attorney, Agent, or Firm—Michael Best & Friedrich LLP

(57) ABSTRACT

A patient monitoring system for acquiring a physiological waveform, and a method of detecting the presence of pacemaker pulses in same. The patient monitoring system includes an input circuit for acquiring an analog ECG, an analog pace detection circuit connected to the input amplifier for generating analog pacemaker pulse markers and energy measures from analog ECG, a digital ECG processing circuit for providing a digitized output of the analog ECG, and software for analyzing the digitized output to establish digital pace detection markers, and for comparing the analog pacemaker pulse markers and energy measures to the digital pace detection markers to eliminate erroneously detected pacemaker pulses. The method includes the acts of acquiring an analog ECG waveform; analyzing the analog ECG waveform to generate first pacemaker pulse markers and energy measures; digitizing the analog ECG waveform to produce digital ECG data; analyzing the digital ECG data to generate second pacemaker pulse markers; comparing the first pacemaker pulse markers and energy measures to the second pacemaker pulse markers; and analyzing the timing relationship between detected pacemaker pulses and certain ECG features to determine the pacing mode of the implanted pacemaker.

20 Claims, 3 Drawing Sheets

METHOD AND APPARATUS FOR AUTOMATICALLY DETECTING AND INTERPRETING PACED ELECTROCARDIOGRAMS

BACKGROUND OF THE INVENTION

The invention relates to patient monitoring and diagnostic devices, and particularly, to patient monitoring and diagnostic devices capable of acquiring multiple-lead electrocardiograph (ECG) signals and performing rhythm analysis on the signals.

It is commonly known in the art to provide patient monitoring and diagnostic devices, particularly multiple-lead capability ECG machines, with the ability to engage in complex ECG rhythm analysis. The rhythm analysis capability is usually a function of the software controlling the machine. Typically, the ECG waveform is filtered, and digitized, i.e., input to an analog-to-digital (A/D) converter. The digitized waveform is then analyzed by the rhythm analysis software. The goal of the rhythm analysis is to make an accurate diagnosis of the cardiac condition of the patient being evaluated.

It is estimated that approximately two to three percent of all patients evaluated using multiple-lead ECG machines have implanted pacemakers that assist the patient's cardiac performance. In order to provide an accurate rhythm analysis, the ECG machine must be able to detect the existence of pacemaker pulses in the ECG waveform and provide to the clinician an indication that the particular event on the ECG waveform is a pacemaker-triggered event, and not an abnormal physiological event, such as an ectopic heartbeat. Pacemaker pulses are typically seen as high frequency spikes on the ECG waveform. The timing relationship of detected pulses to features of the ECG is then used by the algorithm to determine the pacing mode of the implanted pacemaker.

Known patient monitoring and diagnostic systems perform pacemaker pulse detection prior to digitization of the ECG waveform. The detection is performed using analog signal processing techniques. In particular, a high pass filter is used to locate the presence of high frequency elements of the ECG waveform that indicate when a pacemaker pulse has occurred. The information about the detected pacemaker pulse is then passed on to the ECG analysis software by inserting artificial markers in the digitized ECG data wherever a pacemaker pulse is estimated to be. The analysis software then detects these markers and analyzes the ECG waveform with the knowledge that the event markers indicate pacemaker pulses.

SUMMARY OF THE INVENTION

The inventors have determined that there are two major drawbacks to the prior methods of detecting pacemaker pulses in an ECG waveform as set forth above. First, the analog detection circuitry used to detect the high frequency pacemaker pulses is generally susceptible to high frequency noise commonly present in clinical environments. This noise is often falsely identified as being a pacemaker pulse.

Second, because the detected pacemaker pulses are inserted into the digitized ECG waveform data, a high rate of false detection by the analog circuit will corrupt the digitized ECG data. This corruption of the digitized ECG data is irreversible and severely limits the ability of the algorithm and the clinician to accurately analyze the ECG waveform. In order to avoid corrupted data, clinicians often turn "off" the pacemaker detection capability of commonly known patient monitoring and diagnostic systems.

With analog pacemaker detection turned "off," the rhythm analysis software has to rely on the residual pacemaker pulses remaining in the processed, digitized ECG signal. These residual pulses are generally of reduced amplitude and duration due to the low-pass filtering performed in the front-end of the device. This limits the detection performance of the software (low sensitivity). On the other hand, an interpretation algorithm attempting to detect pacemaker pulses with the analog detection turned "off" will rarely detect a false pacemaker pulse (high specificity).

Accordingly, the invention provides a method of analyzing ECG waveforms to detect pacemaker pulses and determine the pacing mode therein. The invention further provides a patient monitoring system employing the method of analyzing ECG waveforms to detect pacemaker pulses therein. The patient monitoring system acquires the physiological waveform from the patient through a front-end instrumentation amplifier. The physiological waveform is simultaneously sent to an analog pace detection circuit and an ECG processing circuit. The analog pace detection circuit includes a high pass filter that detects potential pacemaker pulses in the analog waveform. The high pass filter looks for waveform events that have a high slew rate (high frequency component) that is characteristic of a pacemaker pulse. The analog pace detection circuit transmits analog detection markers along with a measure of the energy contained in each detected pulse to an interpretation algorithm. The interpretation algorithm analyzes the timing of the analog detection markers using timing constraints and the energy of the analog detection markers to help distinguish actual pacemaker pulses from noise or other artifacts that have been erroneously identified as being potential pacemaker pulses. The interpretation algorithm eliminates the erroneously detected detection markers. Stated differently, the interpretation algorithm looks at the analog detection markers and the associated energy measure and eliminates markers that may be due to noise by ignoring consecutive runs, analog detection markers that are very close together in time, and analog markers associated with low-energy pulses. At the same time that the ECG waveform is being processed by the analog pace detection circuit, a second channel of the ECG waveform is input to an ECG processing circuit which filters and digitizes the ECG waveform. The ECG processing circuit outputs the digitized ECG data to the interpretation algorithm.

The pacemaker interpretation algorithm then independently analyzes the digitized ECG data to establish digital pace detection markers that are separate and distinct from the analog detection markers generated by the analog pace detection circuit. These markers are generated based on the detection of the residual pacemaker pulses in the digitized ECG data and are automatically registered by the algorithm as "true" pulses. The analog detection markers are compared with the registered markers from the digitized ECG. Wherever the analog detection markers correspond to the registered markers from the digitized ECG, it is clear that a pacemaker pulse has occurred. However, for each analog detection marker that does not have a corresponding registered marker from the digitized ECG, the digitized ECG data are analyzed locally to search for high-frequency evidence that substantiates the presence of a pacemaker pulse as indicated by the analog detection markers. If such evidence is found, then a new pace detection marker is registered as a "true" pulse.

Following pacemaker pulse detection, the algorithm uses the timing information of the detected pulses and compares it to the timing and morphology of certain ECG features (QRS,P wave, etc.) to determine the pacing mode of the implanted pacemaker.

It is a principal advantage of the invention to provide a highly specific, highly sensitive patient monitoring and diagnostic system for detecting pacemaker pulses in an ECG waveform.

Other features and advantages of the invention are set forth in the following drawings, detailed description and claims.

DETAILED DESCRIPTION OF THE PREFERRED EMBODIMENT

Figure 1:
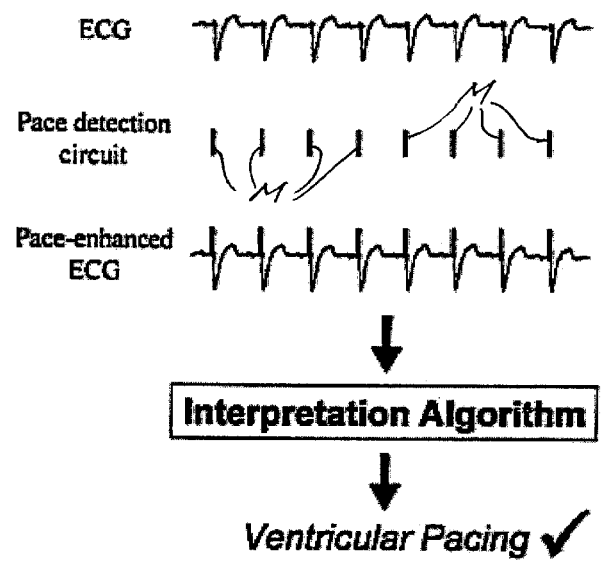
FIG. 1 is a schematic representation of pacemaker pulse detection methods of the prior art.

Shown in FIG. 1 of the drawings is the process by which the prior art electrocardiographs detect and display paced electrocardiograms (ECGs). As shown in FIG. 1, the electrocardiograph acquires the ECG waveform and inputs the ECG waveform to a paced detection circuit. The paced detection circuit analyzes the ECG waveform and generates pacemaker pulse markers in response to the detection of ECG waveform components that have characteristics of pacemaker pulses. The pacemaker pulse markers are added to the ECG waveform to produce a "pace-enhanced" ECG waveform which is input to the ECG interpretation algorithm. The interpretation algorithm provides a clinical analysis of the "pace-enhanced" ECG waveform. In the case shown in FIG. 1, the interpretation algorithm has correctly determined that the patient that is the subject of the ECG waveform is experiencing ventricular pacing.

Figure 2:
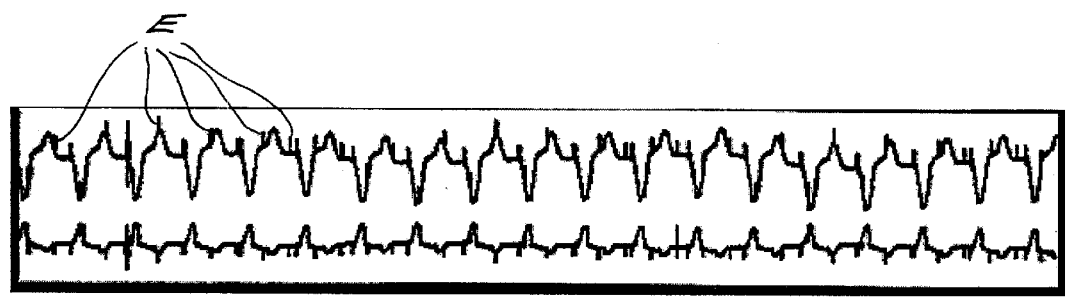
FIG. 2 illustrates an example of an ECG waveform corrupted by falsely detected pacemaker pulses using a pulse detection method of the prior art.

However, the use of pacemaker pulse detection circuits of the prior art can result in the production of corrupt data. In particular, and as shown in FIG. 2, the ECG waveform can be corrupted if the pacemaker pulse detection circuit falsely identifies ambient noise in the clinical environment as a pacemaker pulse. Some of the erroneously detected pacemaker pulses are identified as marker "E" in FIG. 2. The false detection results in the insertion of an errant pacemaker pulse marker in the ECG waveform. As shown in FIG. 2, the ECG waveform is corrupted by falsely detected pacemaker pulses generated using a pace detection circuit and interpretation algorithm of the prior art.

Figure 3:
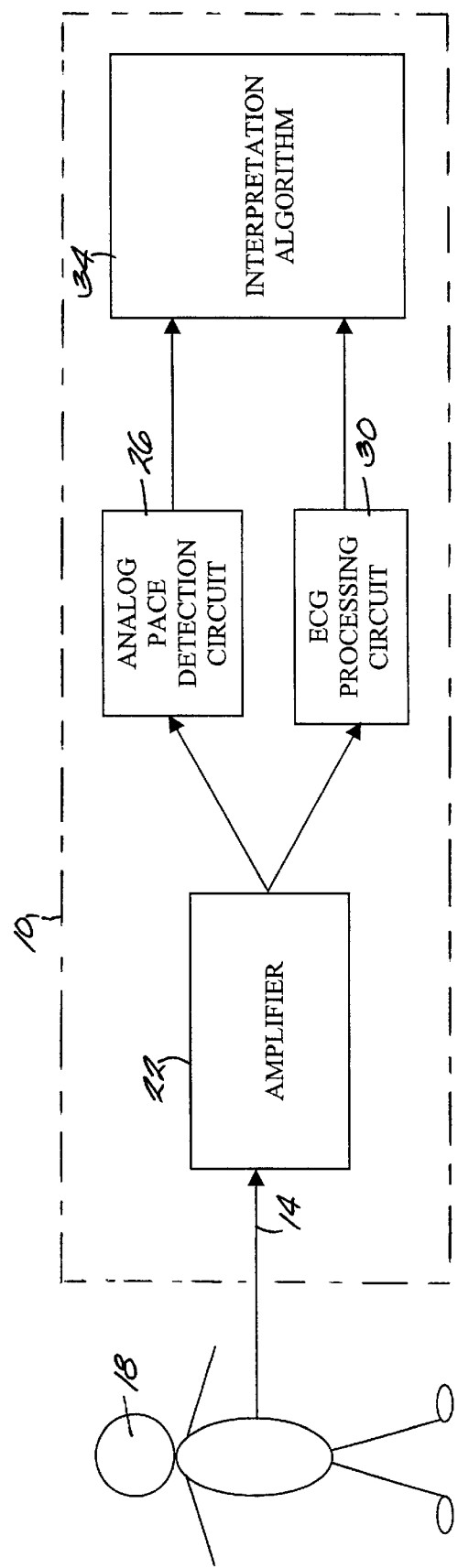
FIG. 3 is a block diagram schematically illustrating a patient monitoring system embodying the invention.

FIG. 3 illustrates a patient monitoring system embodying the invention. While the patient monitoring system can include any patient monitor that acquires an electrocardiogram or ECG waveform, the patient monitoring system of the preferred embodiment is a multiple lead electrocardiograph machine 10. The electrocardiograph 10 includes a lead-set 14 having a plurality of electrodes (not shown) connected to the patient 18. It is commonly known that ECG monitoring may be conducted using 3, 5, 12 or more lead-sets. The electrodes are connected to a front end or instrumentation amplifier 22 which receives the physiological electrical activity from the electrodes and amplifies the analog ECG waveform. The analog ECG waveform is then fed simultaneously to an analog pace detection circuit 26 and to an ECG processing circuit 30.

The analog pace detection circuit 26 includes a high pass filter. The high pass filter detects potential pacemaker pulses in the analog waveform. The high pass filter passes ECG waveform components that have a very high slew rate (or high frequency component) that is characteristic of a common pacemaker pulse. The analog pace detection circuit 26 transmits analog detection markers indicating the position of the detected potential pacemaker pulses along with a measure of the energy contained in each detected pulse to an interpretation algorithm 34. Some of the analog detection markers may be errors that are the result of high frequency noise from the ambient environment. The interpretation algorithm 34 applies timing and energy level constraints to the analog detection markers to help distinguish actual pacemaker pulses from noise or other artifacts that have been erroneously identified as being potential analog pacemaker pulses. In particular, the interpretation algorithm 34 analyzes the analog detection markers, and eliminates those markers that may be due to noise by ignoring consecutive runs, analog detection markers that are very close together in time, and analog markers associated with low-energy pulses.

Simultaneously, the ECG processing circuit 30 filters and digitizes the analog ECG waveform. The ECG processing circuit 30 outputs the digitized ECG data to the interpretation algorithm 34 on a second channel.

The pacemaker interpretation algorithm 34 then independently analyzes the digitized ECG data to generate pace detection markers that are separate and distinct from the analog detection markers generated by the analog pace detection circuit 26. These markers are automatically registered by the algorithm as "true" pacemaker pulses. The analog detection markers are compared with the registered markers from the digitized ECG. Wherever an analog detection marker corresponds to a registered marker from the digitized ECG, it is clear that a pacemaker pulse has occurred. However, for each analog detection marker that does not have a corresponding registered marker from the digitized ECG, the digitized ECG data are analyzed locally to search for high-frequency evidence that substantiates the presence of a pacemaker pulse as indicated by the analog detection markers. If such evidence is found, then a new pace detection marker is registered as a "true" pulse.

Figure 4:
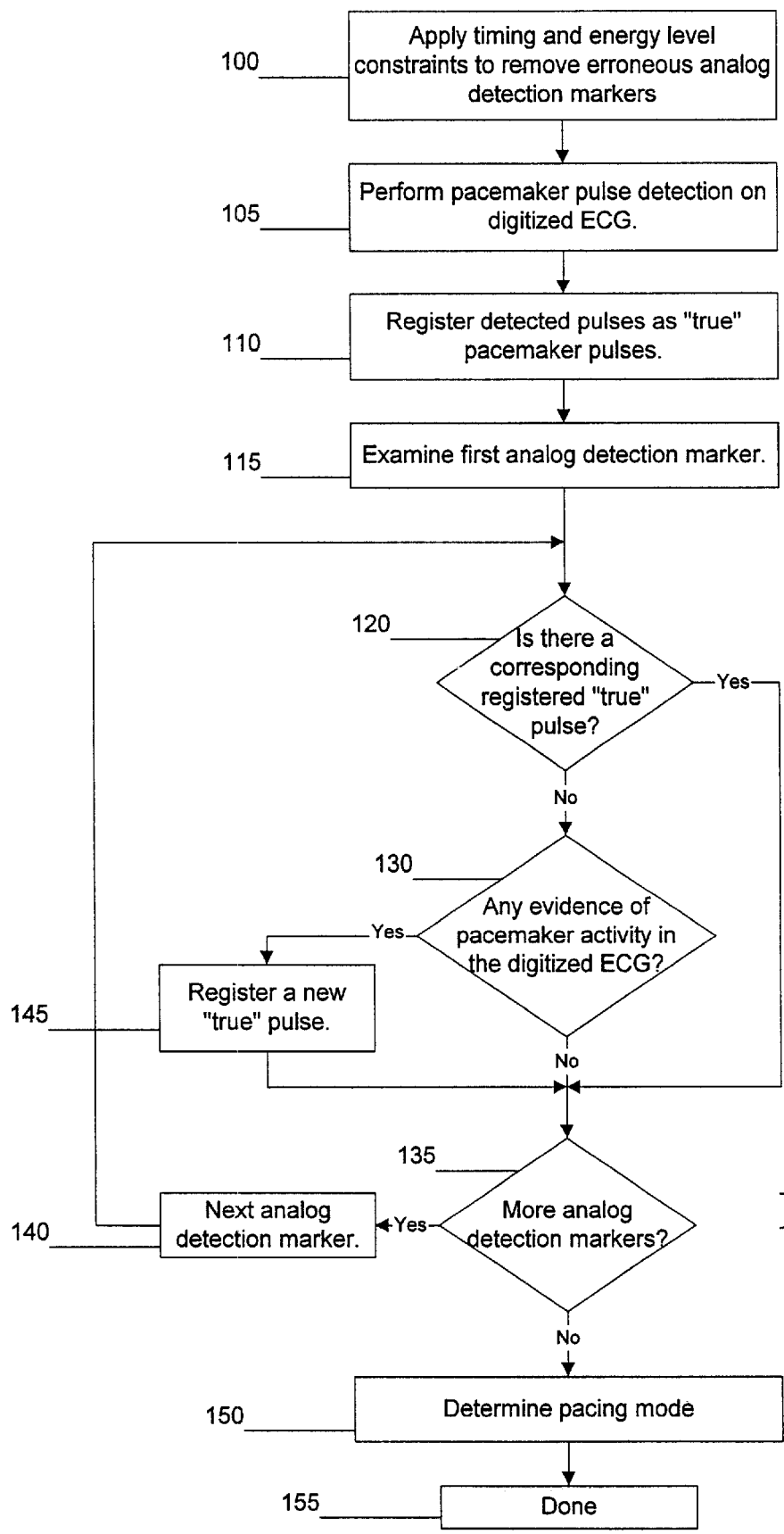
FIG. 4 is a flow chart of the interpretation algorithm pacemaker pulse detection logic.

FIG. 4 illustrates the acts performed in the method of the invention. In particular, the interpretation algorithm applies timing and energy level constraints to remove erroneous analog detection markers 100. The interpretation algorithm then performs pacemaker pulse detection on the digitized ECG lead data 105 and registers the detected pulses as "true" pacemaker pulses 110. Next, the first analog detection marker is examined 115 and is compared 120 to the registered detection markers to determine if there is a "true" pacemaker pulse corresponding to the analog detection marker. For every analog detection marker not corresponding to a registered marker, the ECG waveform is analyzed to determine whether there is any evidence of pacemaker activity in the digitized ECG lead data 130. If there is no such evidence, and, as determined in act 135, there are additional analog detection markers, then the process simply repeats itself 140 for the next analog detection marker. If, on the other hand, there is evidence of pacemaker activity, then a "true" pacemaker pulse is registered 145. Again, if there are more analog detection markers to be examined 135, the process repeats 140 for the next analog detection marker. After interrogating all analog detection markers in the above manner, the timing relationship between the registered "true" pulses and certain features of the ECG (QRS, P wave, etc.) is used to determine the pacing mode 150 of implanted pacemaker. This completes the process 155.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Various features and advantages of the invention are set forth in the following claims.

What is claimed is:

1. A patient monitoring system comprising:
   an input circuit for acquiring an analog ECG signal;
   an analog pace detection circuit connected to the input circuit for generating analog pacemaker pulse markers from the analog ECG;
   a digital ECG processing circuit for providing a digitized output of the analog ECG;
   means for analyzing the digitized output to establish digital pace detection markers;
   means for comparing the analog pacemaker pulse markers to the digital pace detection markers to eliminate erroneously detected pacemaker pulses; and
   means for eliminating erroneously detected analog detection markers based on timing and energy content information.

2. The patient monitoring system as set forth in claim 1, wherein said input circuit includes an amplifier.

3. The patient monitoring system as set forth in claim 1, wherein said digital ECG processing circuit includes an A/D converter.

4. The patient monitoring system as set forth in claim 1, wherein the patient monitoring system is an electrocardiograph.

5. The patient monitoring system as set forth in claim 1, wherein the analog pace detection circuit also generates a measure of the energy of each analog pacemaker pulse marker.

6. A method of detecting pacemaker pulses in an ECG waveform, the method comprising the acts of:
   acquiring an analog ECG waveform;
   analyzing the analog ECG waveform to generate first pacemaker pulse markers;
   analyzing timing information and energy content of the first pacemaker pulse markers to eliminate erroneous pacemaker pulse markers;
   digitizing the analog ECG waveform to produce digital ECG data;
   analyzing the digital ECG data to generate second pacemaker pulse markers; and
   comparing the first pacemaker pulse markers to the second pacemaker pulse markers.

7. The method as set forth in claim 6 wherein the method further comprises the act of comparing the first pacemaker pulse markers to timing and energy level constraints to eliminate erroneously detected pulse markers.

8. The method as set forth in claim 6 wherein the method further comprises the act of examining the digital ECG data to detect pacemaker pulses.

9. The method as set forth in claim 8 wherein the method further comprises the act of adding a pacemaker pulse marker in response to detected pacemaker pulse.

10. The method as set forth in claim 6 wherein the act of analyzing the analog ECG waveform includes the act of generating a measure of the energy of each analog pacemaker pulse marker.

11. A software program for a patient monitoring system capable of acquiring an ECG, the software program performing the acts of:
    acquiring an analog ECG waveform;
    analyzing the analog ECG waveform to generate first pacemaker pulse markers;
    digitizing the analog ECG waveform to produce digital ECG data;
    analyzing the digital ECG data to generate second pacemaker pulse markers; and
    comparing the first pacemaker pulse markers to the second pacemaker pulse markers.

12. The software program as set forth in claim 11 wherein the method further comprises the act of comparing the first pacemaker pulse markers to timing constraints to eliminate erroneously detected pulse markers.

13. The software program as set forth in claim 11 wherein the method further comprises the act of examining the digital ECG data to detect pacemaker pulses.

14. The software program as set forth in claim 11 wherein the method further comprises the act of adding a pacemaker pulse marker in response to detected pacemaker pulses.

15. The software program as set forth in claim 11 wherein the act of analyzing the analog ECG waveform includes the act of generating a measure of the energy of each analog pacemaker pulse marker.

16. A patient monitoring system comprising:
    an input circuit for acquiring an analog ECG;
    an analog pace detection circuit connected to the input circuit for generating analog pacemaker pulse markers from analog ECG;
    a digital ECG processing circuit for providing a digitized output of the analog ECG; and
    software for analyzing the digitized output to establish digital pace detection markers, and for comparing the analog pacemaker pulse markers to the digital pace detection markers to eliminate erroneously detected pacemaker pulses.

17. The patient monitoring system as set forth in claim 16, wherein said input circuit includes an amplifier.

18. The patient monitoring system as set forth in claim 16, wherein said digital ECG processing circuit includes an A/D converter.

19. The patient monitoring system as set forth in claim 16, wherein the patient monitoring system is an electrocardiograph.

20. The patient monitoring system as set forth in claim 16, where the analog pace detection circuit also generates a measure of the energy of each analog pacemaker pulse marker.

* * * * *